United States Patent
Yen

(10) Patent No.: US 10,115,905 B2
(45) Date of Patent: *Oct. 30, 2018

(54) ORGANIC COMPOUND FOR ORGANIC ELECTROLUMINESCENCE DEVICE AND USING THE SAME

(71) Applicant: Feng-Wen Yen, Taipei (TW)

(72) Inventor: Feng-Wen Yen, Taipei (TW)

(*) Notice: Subject to any disclaimer, the term of this patent is extended or adjusted under 35 U.S.C. 154(b) by 114 days.

This patent is subject to a terminal disclaimer.

(21) Appl. No.: 14/860,732

(22) Filed: Sep. 22, 2015

(65) Prior Publication Data

US 2017/0084842 A1    Mar. 23, 2017

(51) Int. Cl.

| | |
|---|---|
| *H01L 51/00* | (2006.01) |
| *H01L 27/32* | (2006.01) |
| *C09K 11/02* | (2006.01) |
| *C07C 13/62* | (2006.01) |
| *C09K 11/06* | (2006.01) |
| *C07C 1/32* | (2006.01) |
| *H01L 51/50* | (2006.01) |

(52) U.S. Cl.
CPC .......... *H01L 51/0056* (2013.01); *C07C 1/321* (2013.01); *C07C 13/62* (2013.01); *C09K 11/06* (2013.01); *H01L 27/3244* (2013.01); *H01L 51/0054* (2013.01); *H01L 51/0058* (2013.01); *C07C 2603/54* (2017.05); *C09K 2211/1011* (2013.01); *H01L 51/5016* (2013.01); *H01L 51/5024* (2013.01); *H01L 51/5036* (2013.01)

(58) Field of Classification Search
CPC ..... C07C 13/62; C07C 1/321; C07C 2603/54; C09K 11/025; C09K 11/06; C09K 2211/1011; H01L 51/0054; H01L 51/0056; H01L 51/0058; H01L 51/5016; H01L 51/5024; H01L 51/5036; H01L 27/3244

See application file for complete search history.

(56) References Cited

U.S. PATENT DOCUMENTS

| | | | |
|---|---|---|---|
| 8,962,160 B2 | 2/2015 | Yen et al. | |
| 8,993,130 B2 | 3/2015 | Yen et al. | |
| 9,048,437 B2 | 6/2015 | Yen et al. | |
| 9,698,351 B2 * | 7/2017 | Yen | H01L 51/006 |
| 2013/0048975 A1 | 2/2013 | Hong et al. | |
| 2014/0151645 A1 | 6/2014 | Yen et al. | |
| 2014/0175383 A1 | 6/2014 | Yen et al. | |
| 2016/0218292 A1 * | 7/2016 | Yen | H01L 51/0056 |
| 2016/0218293 A1 * | 7/2016 | Yen | H01L 51/0056 |
| 2016/0343941 A1 * | 11/2016 | Yen | H01L 51/006 |

FOREIGN PATENT DOCUMENTS

| | | |
|---|---|---|
| WO | 2008062636 A1 | 5/2008 |
| WO | 2012091471 A2 | 7/2012 |

* cited by examiner

*Primary Examiner* — Dawn Garrett

(57) ABSTRACT

The present invention generally discloses an organic compound and organic electroluminescence (herein referred to as organic EL) device using the organic compound. More specifically, the present invention relates to an organic EL device employing the organic compound as fluorescent emitting layer which can display long lifetime, high efficiency and emitting fluorescent blue light and green light.

9 Claims, 1 Drawing Sheet

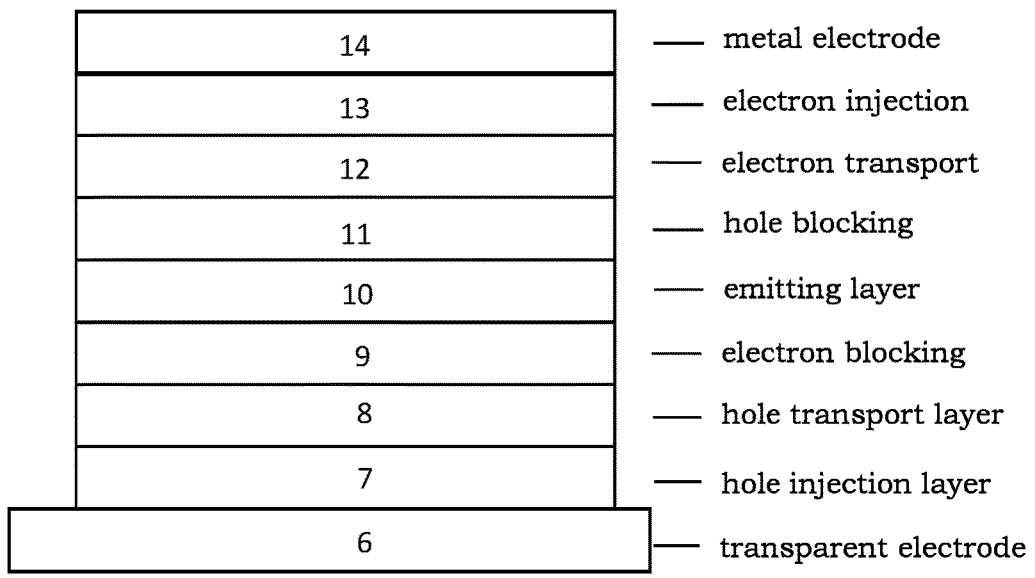

ORGANIC COMPOUND FOR ORGANIC ELECTROLUMINESCENCE DEVICE AND USING THE SAME

FIELD OF INVENTION

The present invention generally relates to an organic compound and organic electroluminescence (herein referred to as organic EL) device using the organic compound. More specifically, the present invention relates to an organic EL device employing the organic compound as fluorescent emitting layer which can display long lifetime, high efficiency and emitting blue light.

BACKGROUND OF THE INVENTION

Organic EL device has many advantages such as self-emitting, wider viewing angles, faster response speeds and highly luminescence. Their simpler fabrication and capable of giving clear display comparable with LCD, making organic EL device an industry display of choice. Organic EL device contain emitting materials which are arranged between a cathode and a anode, when a applied driving voltage is added, an electron and a hole were injected into the emitting layer and recombined to form an exciton. The exciton which results from an electron and a hole recombination have a singlet spin state or triplet spin state. Luminescence from a singlet spin state emits fluorescence and luminescence from triplet spin state emits phosphorescence.

Organic EL device are generally composed of functionally divided organic multi-layers, e.g., hole injection layer (HIL), hole transporting layer (HTL), emitting layer (EML), electron transporting layer (ETL) and electron injection layer (EIL) and so on. A emitting material have good charge carrier mobility and excellent operational durability can lower driving voltage and power consumption, increasing efficiency and half-life time of organic EL device.

For full-colored flat panel displays in AMOLED, the compound used for the blue emitting layer are still unsatisfactory in half-life time and efficiency. Many compounds are used for fluorescent blue host in emitting layer. U.S. Pat. No. 5,935,721 used 9,10-di(naphthalen-2-yl)anthracene (AND) as blue host in emitting layer. U.S. Pat. No. 7,691,492 used 1,1-(9,9-dimethyl-9H-fluorene-2,7-diyl)dipyrene (DFDP) as host for blue organic EL device. These compounds still have disadvantages for industrial practice use.

In the prior invention U.S. Pat. No. 9,048,437B2, Yen et al. employ an indenotriphenylene skeleton link to a heteroaryl group substituted naphthyl anthracene group to finish the fluorescent blue emitting compounds. In the present invention, for the purpose to prolong the half-life time and improve efficiency for fluorescent blue emitting organic EL device we employ an indenotriphenylene skeleton link to a fused ring hydrocarbon units with two to four rings substituted phenyl anthracene group can display higher half-life time and efficiency than the prior invention.

SUMMARY OF THE INVENTION

In accordance with the present invention, the organic compound and their use as emitting material for organic EL device are provided. The organic compound can overcome the drawbacks of the conventional material like as shorter half-life time and lower efficiency, especially for blue fluorescent emitting compound in the present invention. For full-colored flat panel displays, the blue emitting material is still not satisfied for practice use for its shorter half-life time and efficiency.

An object of the present invention is to provide the organic compound which can be used as emitting material for organic EL device.

Another object of the present invention is to apply the organic compound for fluorescent blue emitting material of organic EL device and improve the half-life time and efficiency.

The present invention has the economic advantages for industrial practice. Accordingly, the present invention discloses the organic compound which can be used for organic EL device is disclosed. The mentioned organic compound is represented by the following formula (I):

formula (I)

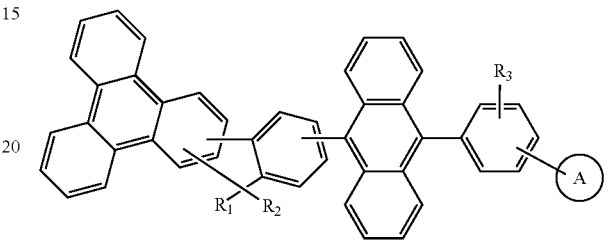

wherein A represents a substituted or unsubstituted fused ring hydrocarbon units with two to four rings group, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

BRIEF DESCRIPTION OF THE DRAWINGS

The FIGURE shows one example of organic EL device in the present invention. 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited onto 11, 13 is electron injection layer which is deposited on to 12.

DESCRIPTION OF THE PREFERRED EMBODIMENTS

What probed into the invention is the organic compound and organic EL device using the organic compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the organic compound which can be used as fluorescent blue emitting material of organic EL device are disclosed. The mentioned compound are represented by the following formula (I):

formula (I)

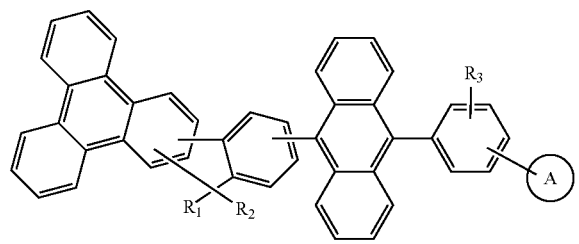

wherein A represents a substituted or unsubstituted fused ring hydrocarbon units with two to four rings group, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

In this embodiment, some organic compounds are shown below:

EX1

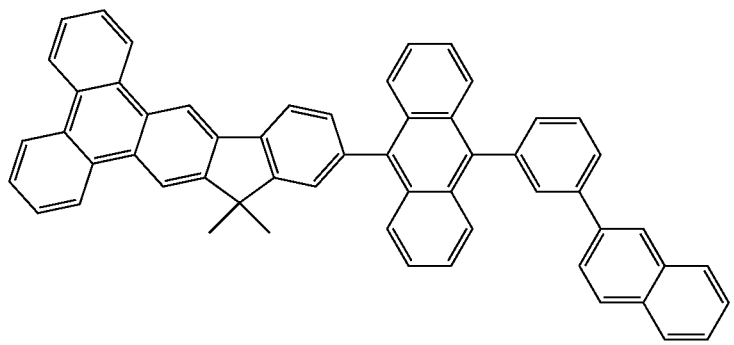

EX2

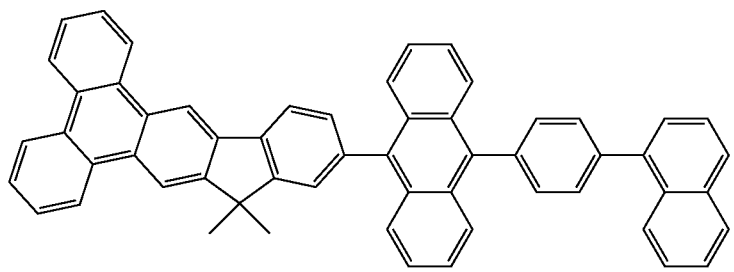

EX3

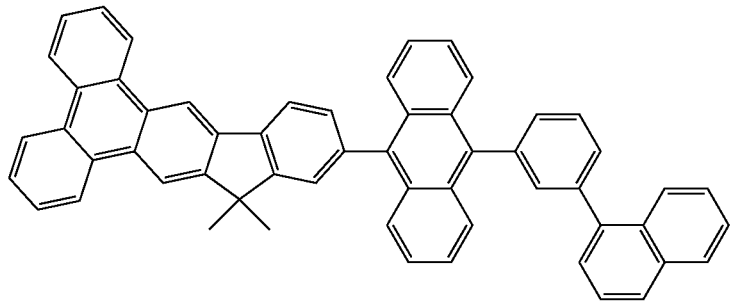

EX4

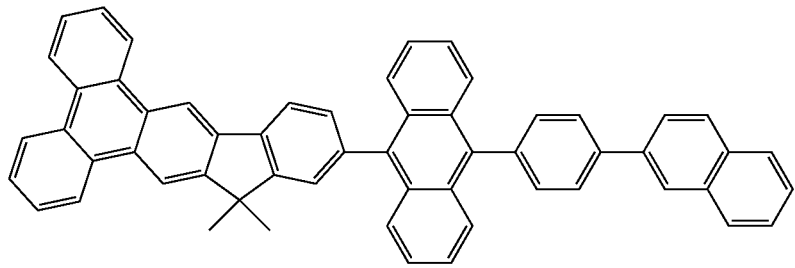

-continued
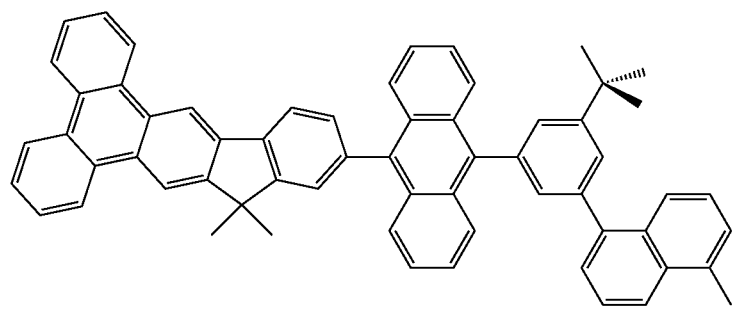
EX5
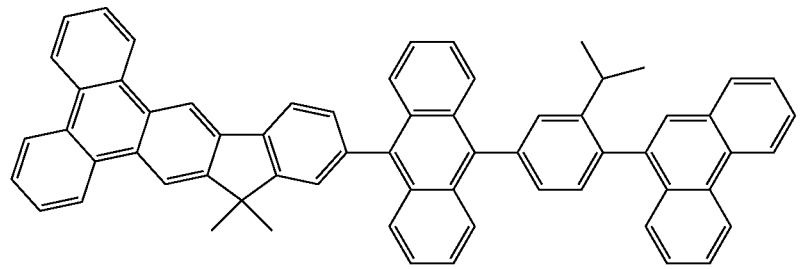
EX6
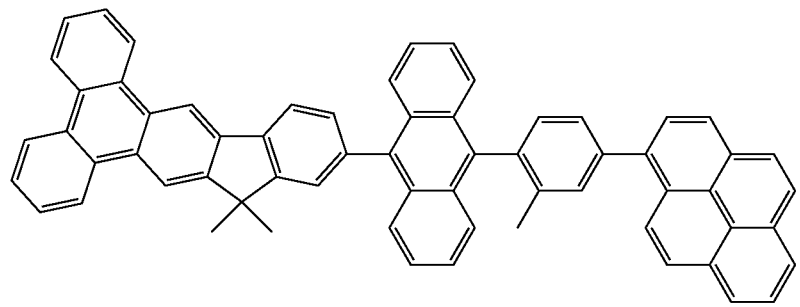
EX7
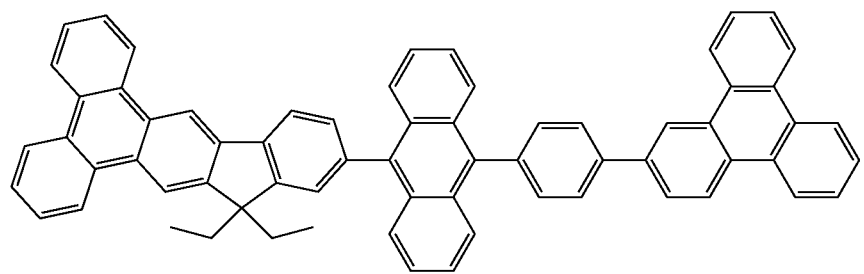
EX8
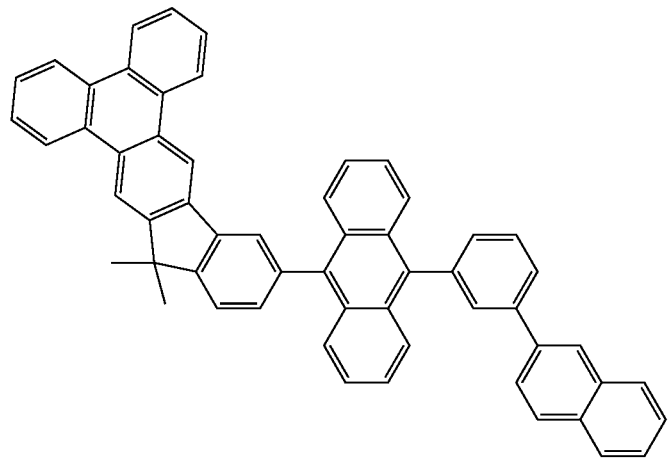
EX9

EX10
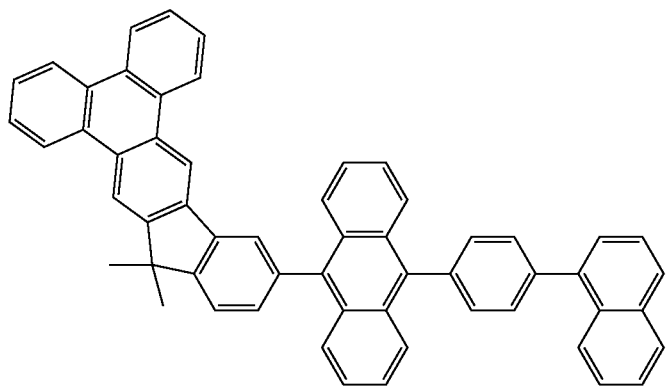
EX11
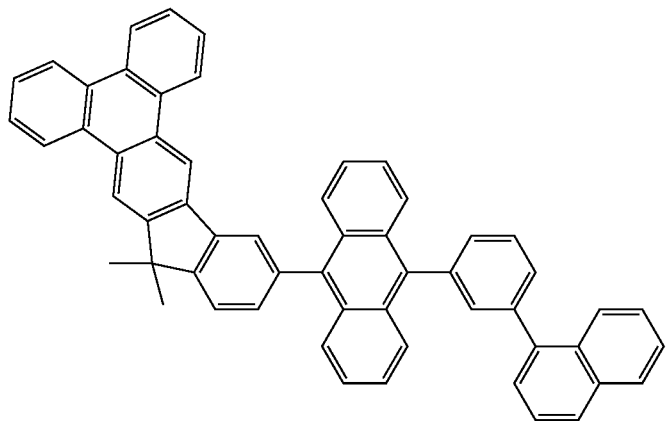
EX12
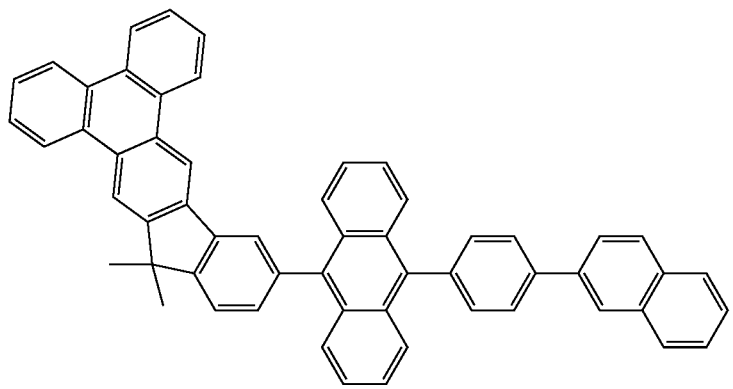
EX13
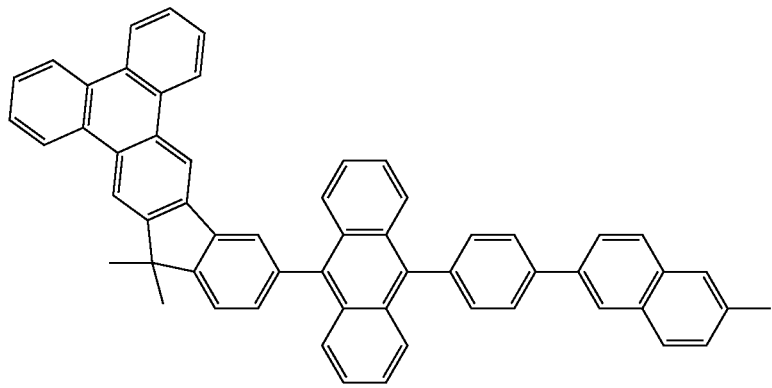

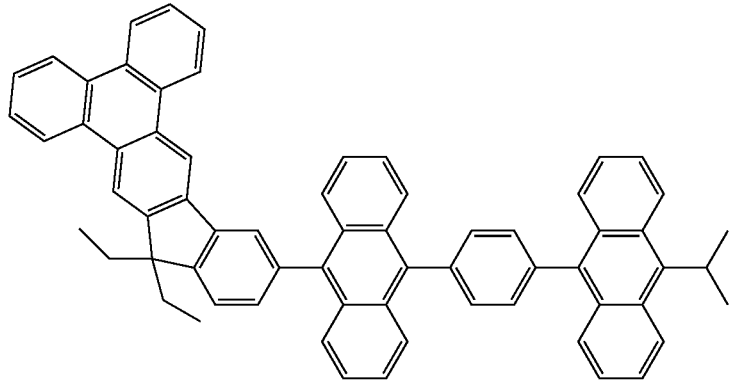
EX14
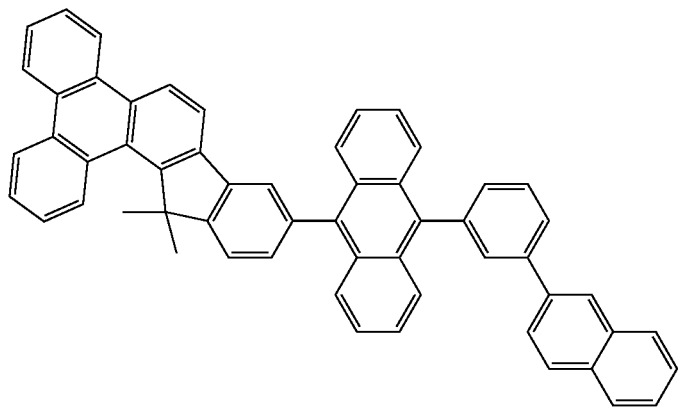
EX15
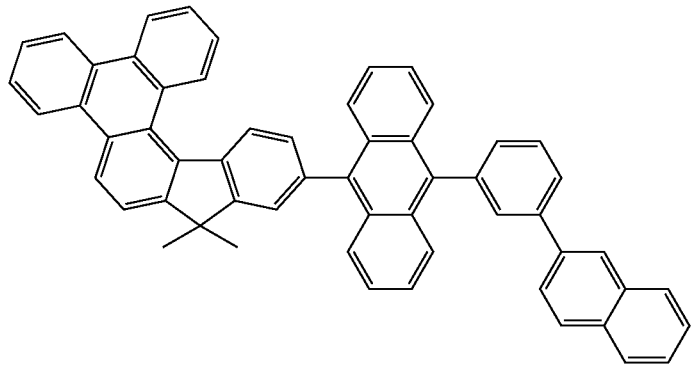
EX16
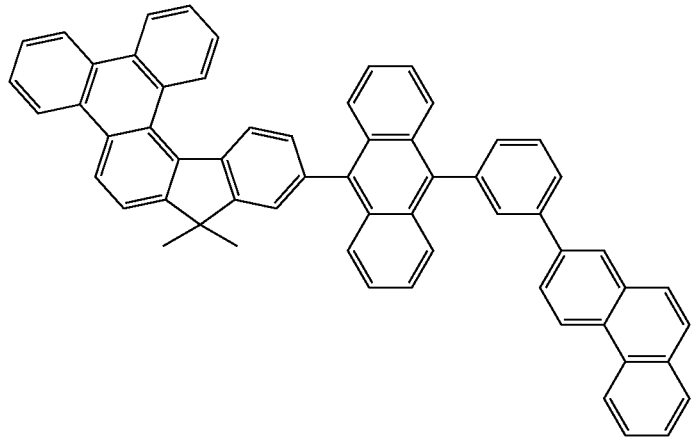
EX17

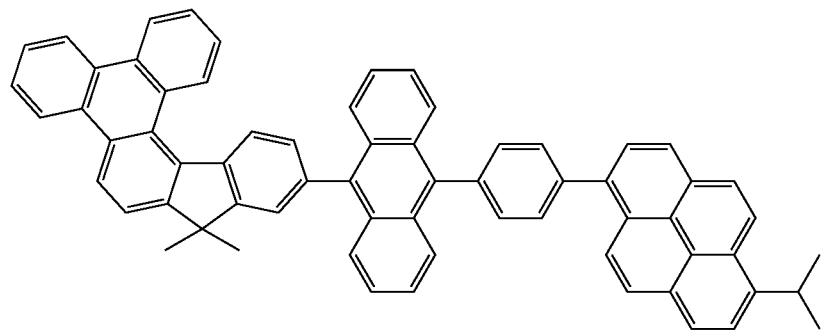
EX18
EX19
EX20
EX21

EX22

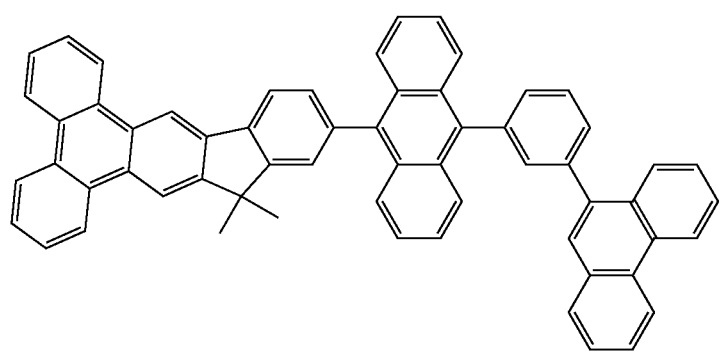

Detailed preparation for the organic compound in the present invention could be clarified by exemplary embodiments, but the present invention is not limited to exemplary embodiments. EXAMPLE 1~4 show the preparation for some EXAMPLES of the organic compound in the present invention. EXAMPLE 5 show the fabrication of organic EL device and I-V-B, half-life time of organic EL device testing report.

Example 1

Synthesis of EX2

Synthesis of 2-(biphenyl-2-yl)-7-bromo-9,9-dimethyl-9H-fluorene

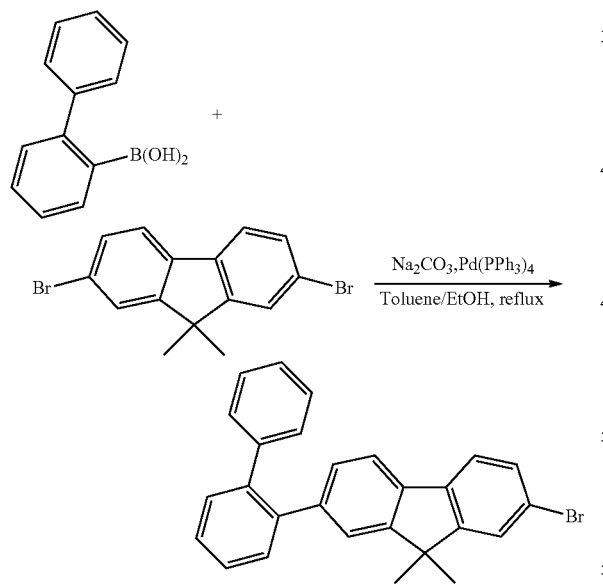

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

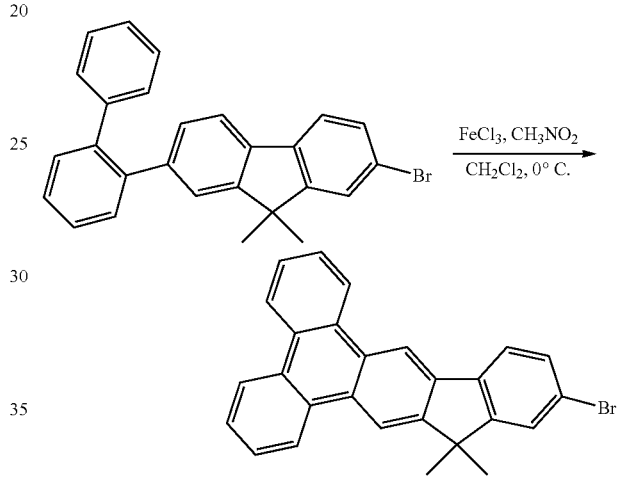

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron(III)chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). $^1$H NMR (CDCl3, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 2-(10,10-dimethyl-10H-indeno[2,1-b]triphenylen-12-yl)-4,4,5,5-tetramethyl-1,3,2-dioxaborolane

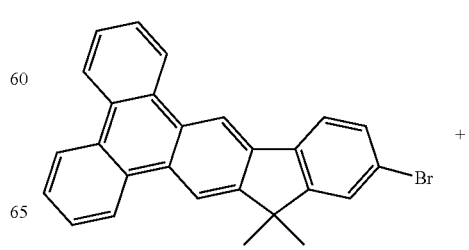

-continued

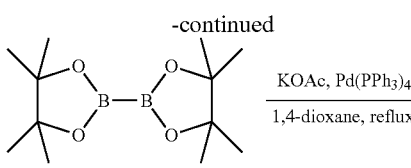

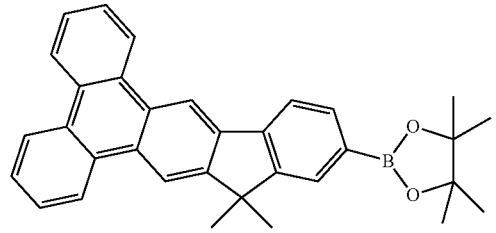

A mixture of 10.7 g (25.3 mmol) of 12-bromo-10,10-dimethyl-10H-indeno-[1,2-b]triphenylene, 7.7 g (30.3 mmol) of bis(pinacolato)diboron, 0.3 g (0.26 mmol) of Pd(PPh₃)₄, 7.4 g (75.4 mmol) of potassium acetate, and 300 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (6.4 g, 13.7 mmol, 54%) as a light-yellow solid; ¹H NMR (CDCl3, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of EX2

Synthesis of 10,10-dimethyl-12-(10-(4-(naphthalen-1-yl)phenyl)anthracen-9-yl)-10H-indeno[2,1-b]triphenylene

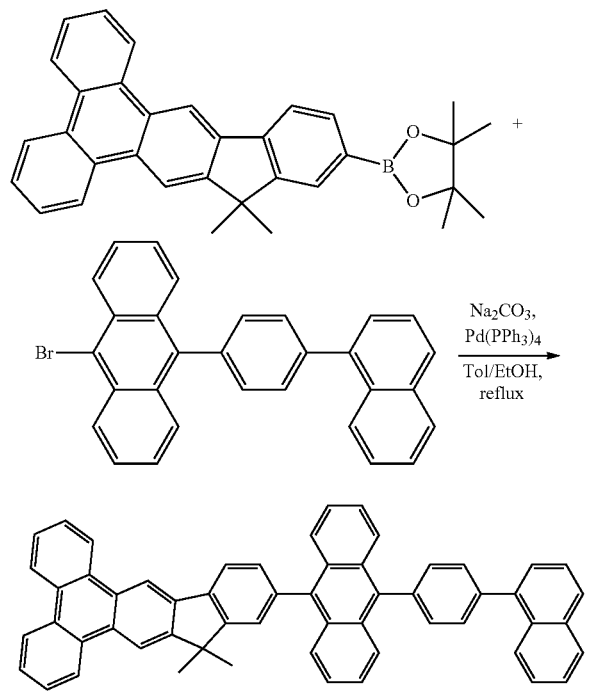

A mixture of 4.7 g (10 mmol) of 2-(10,10-dimethyl-10H-indeno[2,1-b]triphenylen-12-yl)-4,4,5,5-tetramethyl-1,3,2-dioxaborolane, 4.6 g (10 mmol) of 9-bromo-10-(4-(naphthalen-1-yl)phenyl)anthracene, 0.22 g (0.2 mmol) of tetrakis(triphenylphosphine)palladium, 20 ml of 2M Na₂CO₃, 20 ml of EtOH and 50 ml toluene was degassed and placed under nitrogen, and then heated at 90° C. overnight. After finishing the reaction, the mixture was allowed to cool to room temperature. Than 150 ml of MeOH was added, while stirring and the precipitated product was filtered off with suction. To give 4.2 g (yield 58%) of yellow product which was recrystallized from toluene. MS (m/z, FAB⁺): 722.4, ¹H NMR (CDCl₃, 400 MHz): chemical shift (ppm) 9.13 (s, 1H), 8.89 (d, J=7.84 Hz, 1H), 8.83~8.80 (m, 2H), 8.72~8.69 (m, 2H), 8.25 (d, J=7.84 Hz, 1H), 7.88~7.66 (m, 16H), 7.58~7.43 (m, 4H), 7.38~7.32 (m, 5H), 1.79 (s, 6H).

Example 2

Synthesis of EX9

Synthesis of 2-(biphenyl-2-yl)-6-bromo-9,9-dimethyl-9H-fluorene

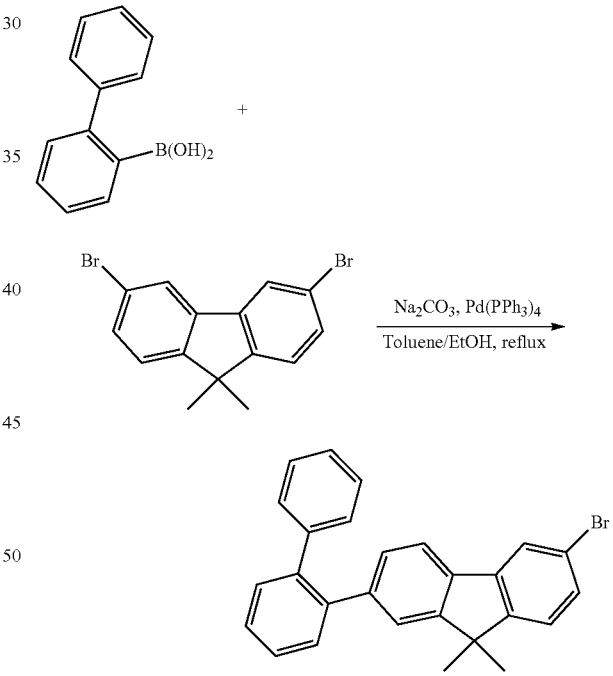

A mixture of 35.2 g (100 mmol) of 3,6-dibromo-9,9-dimethyl-9H-fluorene, 21.8 g (110 mmol) of biphenyl-2-ylboronic acid, 2.31 g (2 mmol) of Pd(PPh₃)₄, 75 ml of 2M Na₂CO₃, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 13-bromo-10,10-dimethyl-10H-indeno[2,1-b]triphenylene

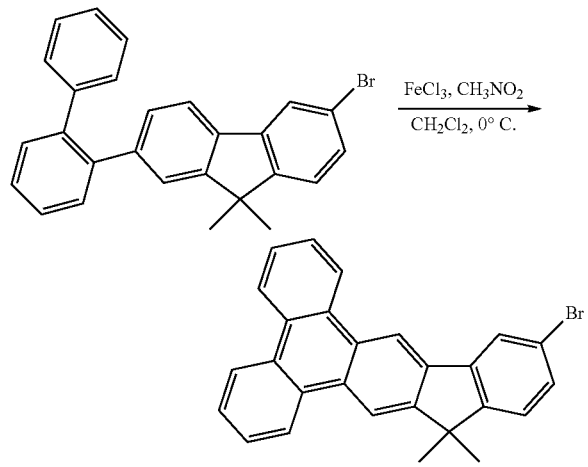

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) iron(III)chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). $^1$H NMR (CDCl$_3$, 500 MHz): chemical shift (ppm) 8.93 (s, 1H), 8.77~8.71 (m, 2H), 8.67~8.65 (m, 3H), 8.08 (d, J=1.5 Hz, 1H), 7.71~7.64 (m, 4H), 7.49 (dd, J$_1$=8.5 Hz, J$_2$=1.5 Hz, 1H), 7.37 (d, J=8.5 Hz, 1H), 1.62 (s, 6H).

Synthesis of 2-(10,10-dimethyl-10H-indeno[2,1-b]triphenylen-13-yl)-4,4,5,5-tetramethyl-1,3,2-dioxaborolane

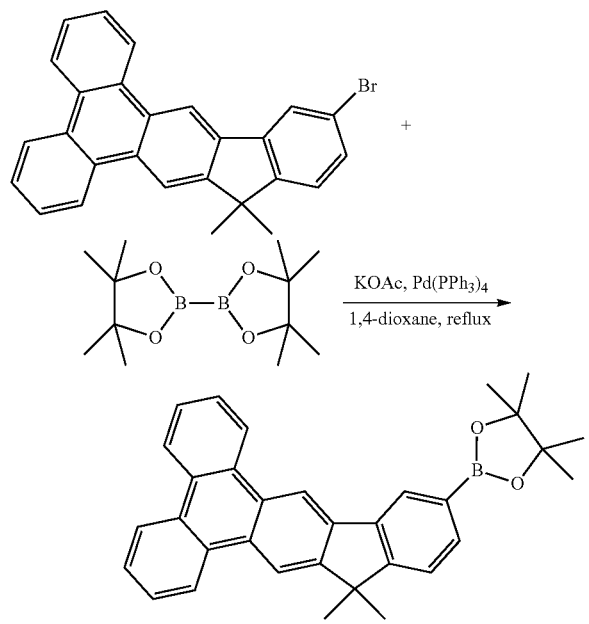

A mixture of 10.7 g (25.3 mmol) of 13-bromo-10,10-dimethyl-10H-indeno[2,1-b]triphenylene, 7.7 g (30.3 mmol) of bis(pinacolato)diboron, 0.3 g (0.26 mmol) of Pd(PPh$_3$)$_4$, 7.4 g (75.4 mmol) of potassium acetate, and 500 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuum. The residue was purified by column chromatography on silica to give product (9.5 g, 20.2 mmol, 80%) as a light-yellow solid; $^1$H NMR (CDCl$_3$, 500 MHz): chemical shift (ppm) 8.93 (s, 1H), 8.77~8.71 (m, 2H), 8.67~8.65 (m, 3H), 7.88 (d, J=1.5 Hz, 1H), 7.71~7.64 (m, 4H), 7.29 (dd, J$_1$=8.5 Hz, J$_2$=1.5 Hz, 1H), 7.42 (d, J=8.5 Hz, 1H), 1.62 (s, 6H), 1.42 (s, 12H).

Synthesis of 10,10-dimethyl-13-(10-(3-(naphthalen-2-yl)phenyl) anthracen-9-yl)-10H-indeno[1,2-b]triphenylene

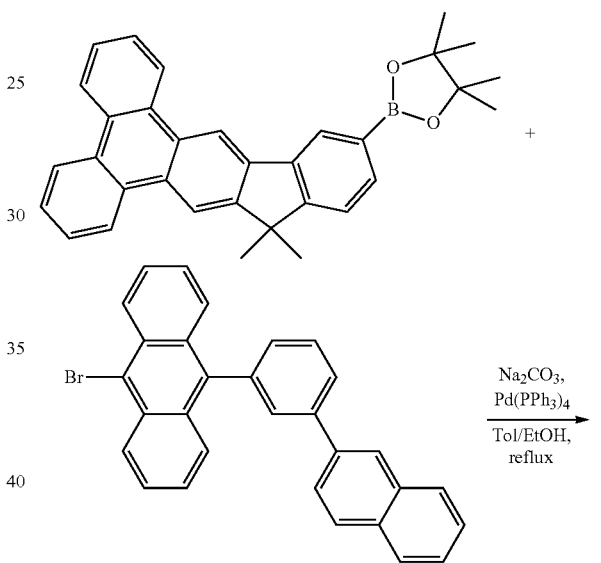

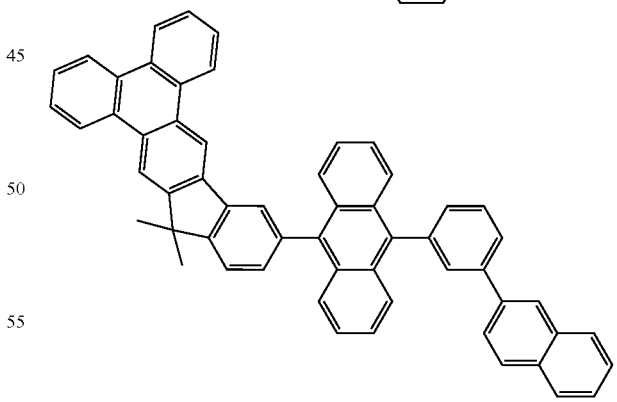

A mixture of 9.5 g (20.2 mmol) of 2-(10,10-dimethyl-10H-indeno[2,1-b]triphenylen-13-yl)-4,4,5,5-tetramethyl-1,3,2-dioxaborolane, 9.6 g (21 mmol) of 9-bromo-10-(3-(naphthalen-2-yl)phenyl)anthracene, 0.44 g (0.4 mmol) of tetrakis(triphenylphosphine)palladium, 30 ml of 2M Na$_2$CO$_3$, 40 ml of EtOH and 100 ml toluene was degassed and placed under nitrogen, and then heated at 90° C. overnight. After finishing the reaction, the mixture was allowed to cool to room temperature. Than 300 ml of MeOH was added, while stirring and the precipitated product was filtered off with suction. To give 4 g (yield 53%) of yellow product which was recrystallized from toluene. MS (m/z, FAB+): 722.1, ¹H NMR (CDCl₃, 400 MHz): chemical shift (ppm) 8.99 (s, 1H), 8.83~8.82 (m, 2H), 8.68~8.65 (m, 3H), 8.21~8.18 (dd, 1H), 8.14 (s, 1H), 7.99~7.47 (m, 20H), 7.41~7.36 (m, 4H), 1.83 (s, 6H).

Example 3

Synthesis of EX10

Synthesis of 10,10-dimethyl-13-(10-(4-(naphthalen-1-yl)phenyl)anthracen-9-yl)-10H-indeno[1,2-b]triphenylene

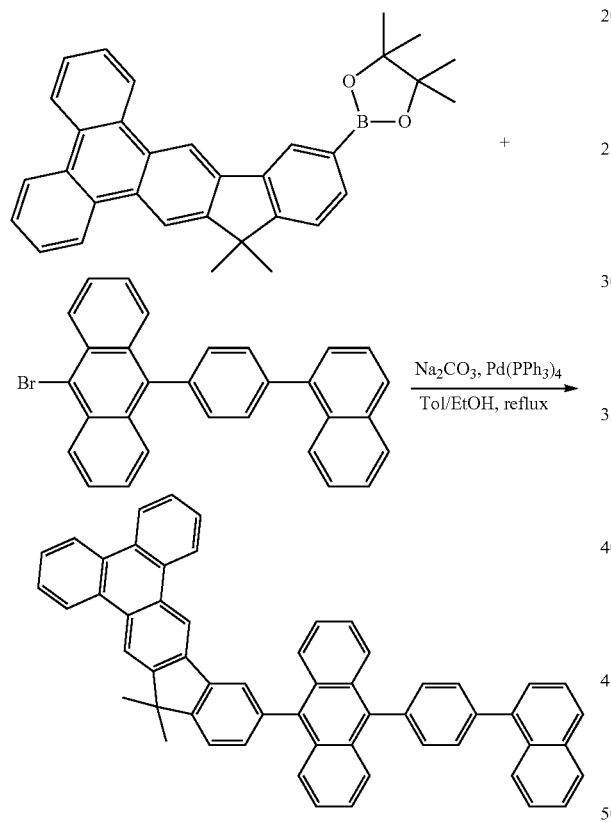

Example 4

Synthesis of EX22

Synthesis of 10,10-dimethyl-12-(10-(3-(phenanthren-9-yl)phenyl)anthracen-9-yl)-10H-indeno[2,1-b]triphenylene

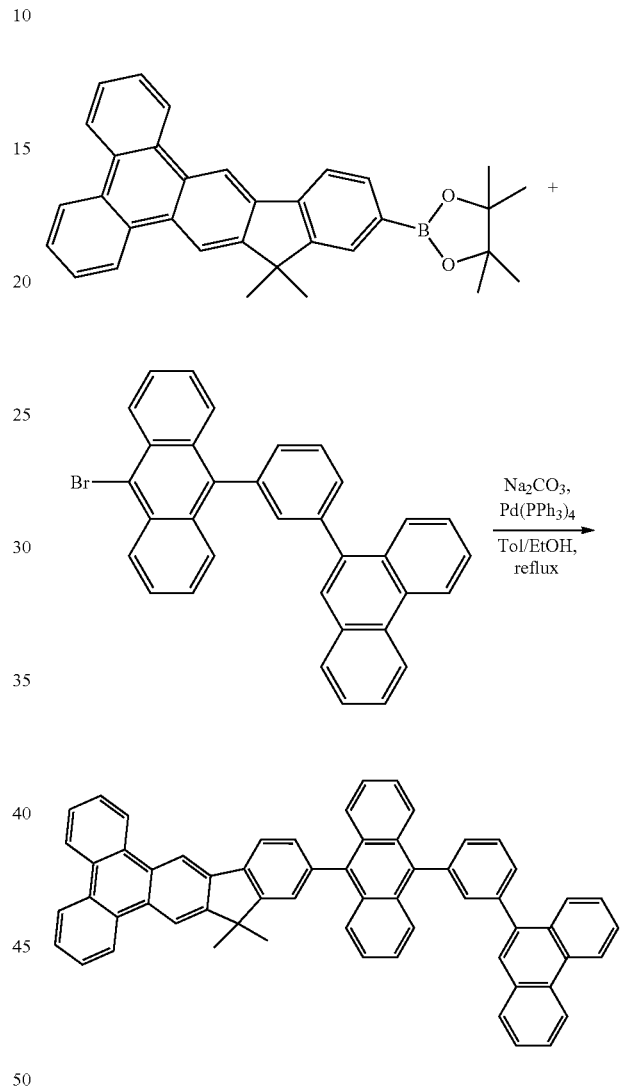

A mixture of 9.5 g (20.2 mmol) of 2-(10,10-dimethyl-10H-indeno[2,1-b]triphenylen-13-yl)-4,4,5,5-tetramethyl-1,3,2-dioxaborolane, 9.6 g (21 mmol) of 9-bromo-10-(4-(naphthalen-1-yl)phenyl)anthracene, 0.44 g (0.4 mmol) of tetrakis(triphenylphosphine)palladium, 30 ml of 2M Na₂CO₃, 40 ml of EtOH and 100 ml toluene was degassed and placed under nitrogen, and then heated at 90° C. overnight. After finishing the reaction, the mixture was allowed to cool to room temperature. Than 300 ml of MeOH was added, while stirring and the precipitated product was filtered off with suction. To give 9.2 g (yield 63%) of yellow product which was recrystallized from toluene. MS (m/z, FAB+): 722.4, ¹H NMR (CDCl₃, 400 MHz): chemical shift (ppm) 8.99 (s, 1H), 8.83~8.80 (m, 2H), 8.70~8.66 (m, 3H), 8.21~8.13 (m, 2H), 7.99~7.51 (m, 20H), 7.45~7.36 (m, 4H), 1.79 (s, 6H).

A mixture of 4.7 g (10 mmol) of 2-(10,10-dimethyl-10H-indeno[2,1-b]triphenylen-12-yl)-4,4,5,5-tetramethyl-1,3,2-dioxaborolane, 5.1 g (10 mmol) of 9-bromo-10-(3-(phenanthren-9-yl)phenyl)anthracene, 0.22 g (0.2 mmol) of tetrakis(triphenylphosphine)palladium, 20 ml of 2M Na₂CO₃, 20 ml of EtOH and 50 ml toluene was degassed and placed under nitrogen, and then heated at 90° C. overnight. After finishing the reaction, the mixture was allowed to cool to room temperature. Than 150 ml of MeOH was added, while stirring and the precipitated product was filtered off with suction. To give 3.0 g (yield 39%) of yellow product which was recrystallized from toluene. MS (m/z, FAB+): 772.6, ¹H NMR (CDCl₃, 400 MHz): chemical shift (ppm) 9.11 (s, 1H), 8.89 (d, J=7.84 Hz, 1H), 8.84~8.78 (m, 4H), 8.71~8.69 (m, 2H), 8.25~8.11 (m, 3H), 7.91~7.64 (m, 15H), 7.58~7.43 (m, 4H), 7.41~7.36 (m, 4H), 1.79 (s, 6H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis (phenyl)-benzidine (NPB) is most widely used as the hole transporting layer. N-(biphenyl-4-yl)-9,9-dimethyl-N-(4'-phenylbiphenyl-4-yl)-9H-fluoren-2-amine (EB2) is used as electron blocking layer, 10,10-dimethyl-12-(10-(naphthalen-2-yl)anthracen-9-yl)-10H-indeno[2,1-b]triphenylene (H1) is used as blue emitting host. N1,N1,N6,N6-tetramtolylpyrene-1,6-diamine (D1) is used as blue guest and N9,N10-diphenyl-N9,N10-dim-tolylanthracene-9,10-diamine (D2) is used as green guest. 2-(10,10-dimethyl-10H-indeno[2,1-b]triphenylen-13-yl)-9-phenyl-1,10-phenanthroline (ET1) is used as electron transporting material to co-deposit with 5% Li, 2-(10,10-dimethyl-1 OH-indeno[2,1-b]triphenylen-12-yl)-4,6-diphenyl-1,3,5-triazine (ET2) is used as hole blocking layer in organic EL device. The prior art of OLED materials for producing standard organic EL device control, comparable materials and EXAMPLES in this invention shown its chemical structure as follows:

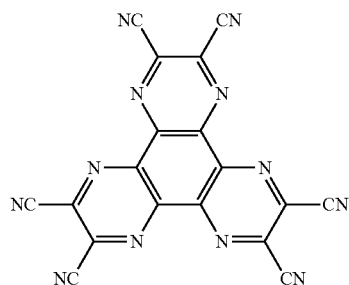

HAT-CN

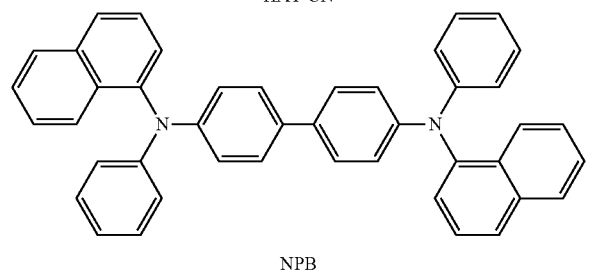

NPB

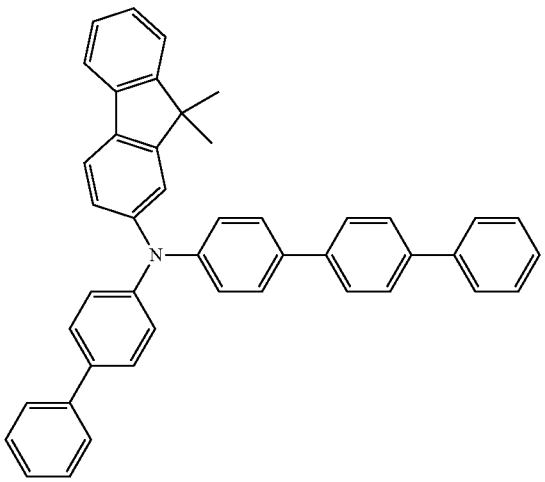

EB2

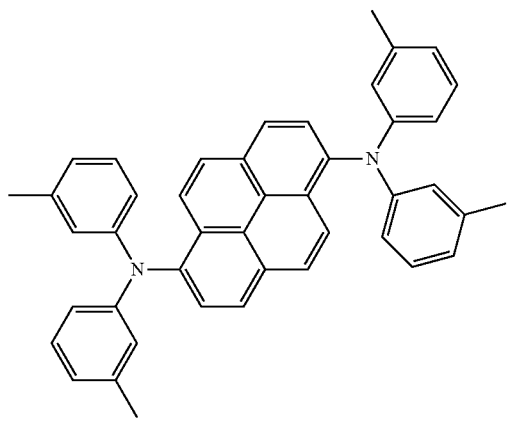

D1

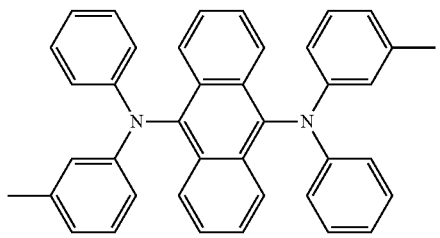

D2

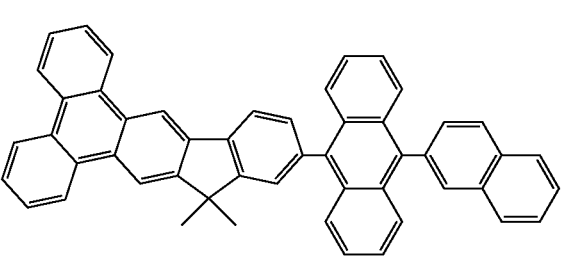

H1

ET1

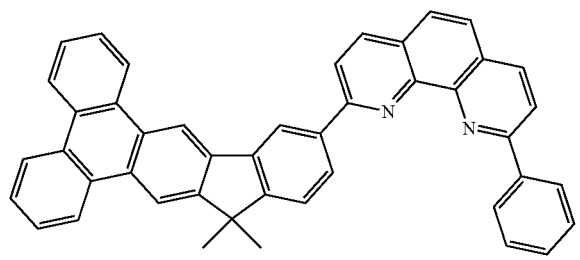

ET2

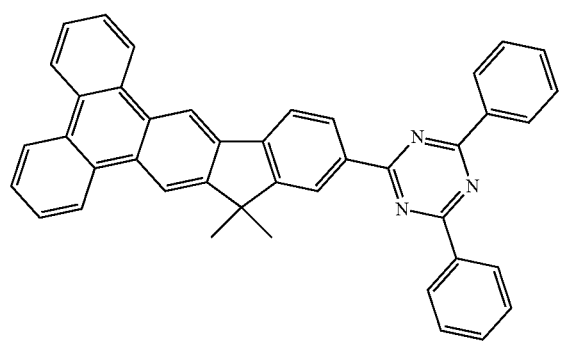

EX2

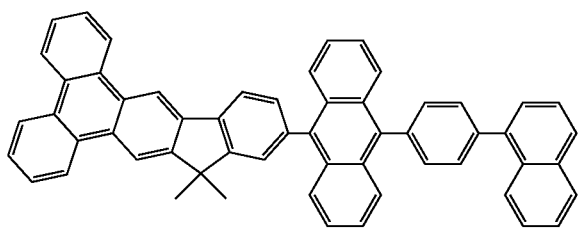

EX9

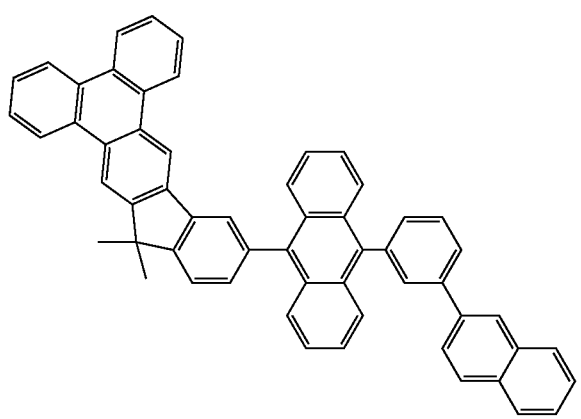

EX10

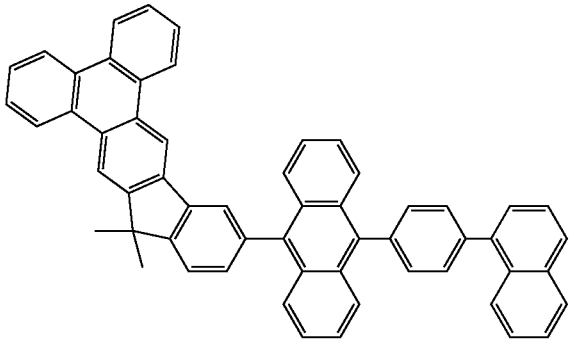

EX22

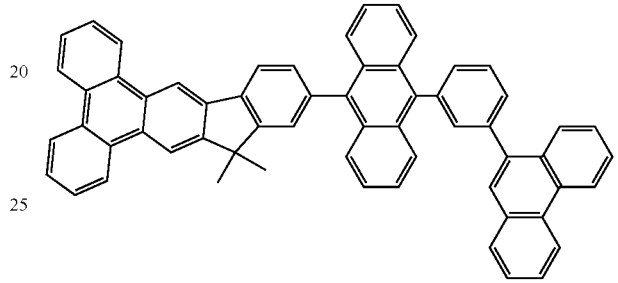

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 5

Using a procedure analogous to the above mentioned general method, fluorescent emitting organic EL device having the following device structure was produced (See the FIGURE): ITO/HAT-CN (10 nm)/NPB (800 nm)/EB2 (5 nm)/host doped D1 or D2 (30 nm)/ET2 (15 nm)/ET1 co-deposit 5% Li (35 nm)/Al (160 nm). The I-V-B (at 1000 nits) and half-life time of fluorescent emitting organic EL device testing report as Table 1. The half-life time is defined that the initial luminance of 4000 cd/$m^2$ has dropped to half.

TABLE 1

| host | Dopant (%) | Voltage (V) | Efficiency (cd/A) | CIE(x, y) | Half-life time(hour) |
|------|------------|-------------|-------------------|-----------|----------------------|
| H1   | 5% D1      | 5.0         | 5.8               | 0.14, 0.18 | 120                  |
| EX2  | 5% D1      | 4.8         | 7.4               | 0.14, 0.17 | 165                  |

TABLE 1-continued

| host | Dopant (%) | Voltage (V) | Efficiency (cd/A) | CIE(x, y) | Half-life time(hour) |
|---|---|---|---|---|---|
| EX9 | 5% D1 | 4.5 | 7.2 | 0.14, 0.17 | 140 |
| EX10 | 5% D1 | 4.7 | 7.5 | 0.14, 0.17 | 168 |
| EX22 | 5% D1 | 4.2 | 7.0 | 0.14, 0.17 | 165 |
| H1 | 9% D2 | 4.5 | 18 | 0.24, 0.62 | 600 |
| EX2 | 9% D2 | 4.0 | 24 | 0.24, 0.61 | 780 |
| EX9 | 9% D2 | 4.1 | 25 | 0.24, 0.62 | 800 |
| EX10 | 9% D2 | 4.0 | 24 | 0.24, 0.62 | 850 |
| EX22 | 9% D2 | 4.5 | 23 | 0.24, 0.59 | 860 |

In the above preferred embodiments for organic EL device test report (see Table 1), we shown that the organic compound with a general formula (I) used as emitting host in the present invention display good performance than the prior art of OLED materials, especially in efficiency and half-life time shown to increase about 30% than the prior invention U.S. Pat. No. 9,048,437B2.

To sum up, the present invention discloses an organic compound which can be used for organic EL device is disclosed. More specifically, an organic EL device employing the organic compound as fluorescent emitting host. The mentioned the organic compound is represented by the following formula (I)

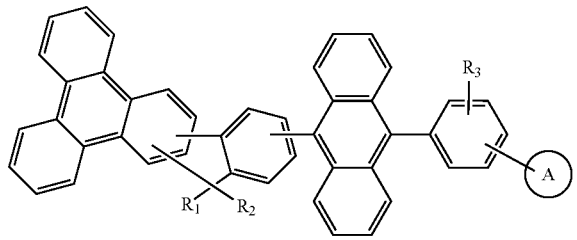

formula (I)

wherein A represents a substituted or unsubstituted fused ring hydrocarbon units with two to four rings group, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. An organic compound with a general formula (I) as follows:

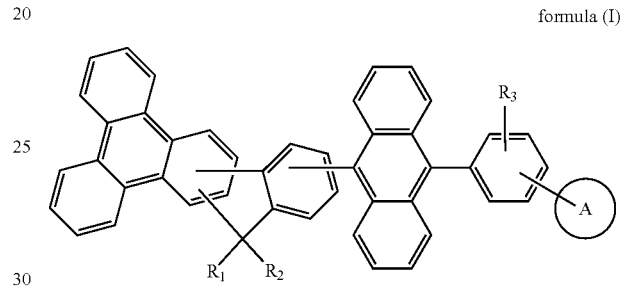

formula (I)

wherein A represents a substituted or unsubstituted fused ring hydrocarbon unit with two to four rings, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

2. The organic compound according to claim 1, wherein the organic compound is selected from the group consisting of:

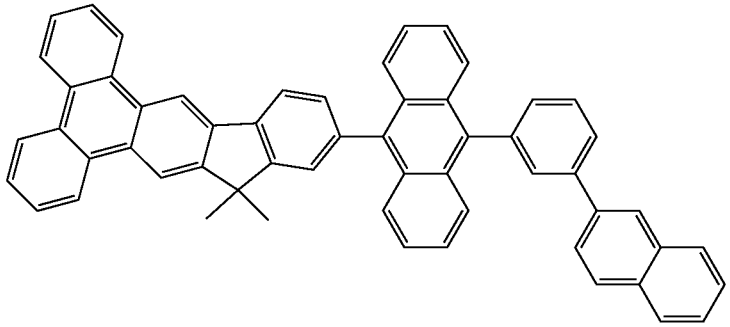

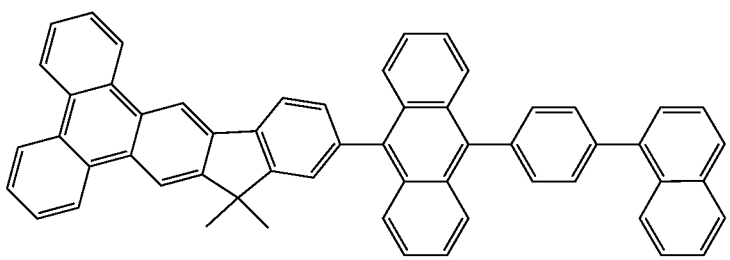

-continued
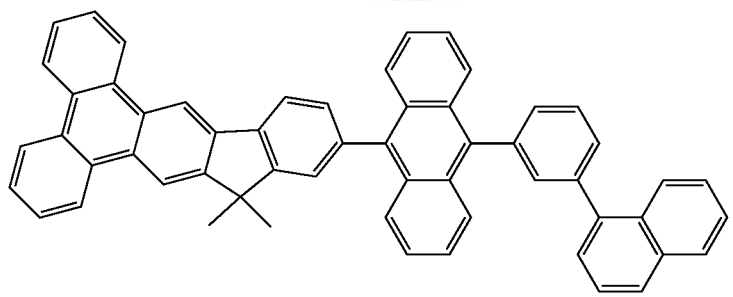
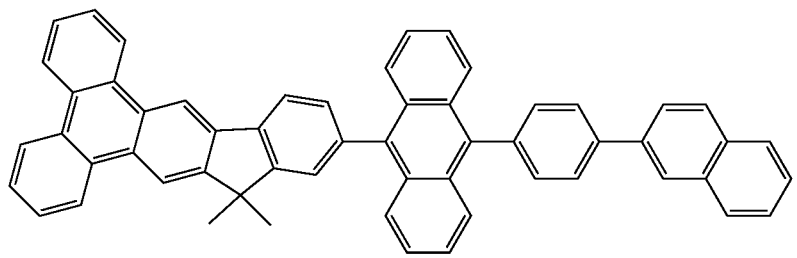
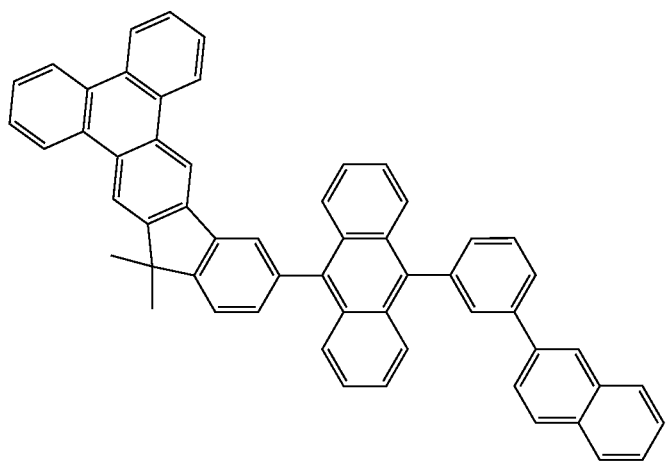
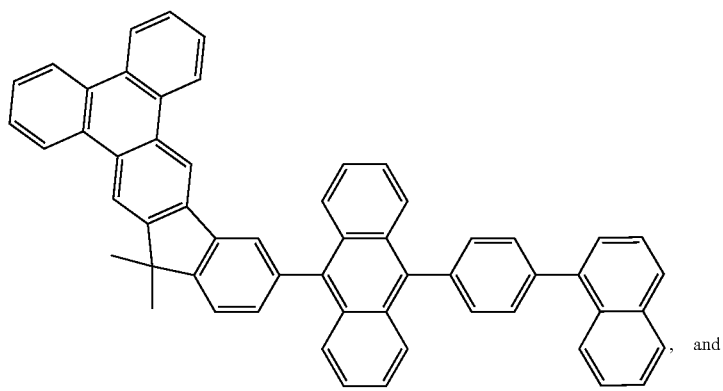
, and

-continued

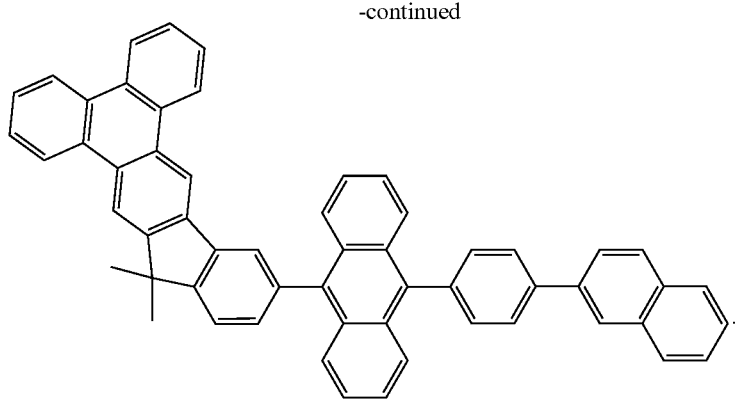

3. A organic electroluminescence device comprising a pair of electrodes consisting of a cathode and an anode, and between the pairs of electrodes comprising at least a light emitting layer, one or more layers of organic thin film layer, wherein the light emitting layer comprising the organic compound according to claim 1.

4. The organic electroluminescence device according to claim 3, wherein the light emitting layer comprising the organic compound with a general formula (1) is a host material.

5. The organic electroluminescence device according to claim 3, wherein the light emitting layer comprising the organic compound with a general formula (1) is a fluorescent emitter.

6. The organic electroluminescence device according to claim 3, wherein the light emitting layer emits fluorescent blue and green lights.

7. The organic electroluminescence device according to claim 3, wherein the device is an organic light emitting device.

8. The organic electroluminescence device according to claim 3, wherein the device is a lighting panel.

9. The organic electroluminescence device according to claim 3, wherein the device is a backlight panel.

* * * * *